(12) United States Patent
Hiley

(10) Patent No.: US 6,245,576 B1
(45) Date of Patent: Jun. 12, 2001

(54) METHOD OF EXPLOSIVES DETECTION

(75) Inventor: Robin Walter Hiley, Farnborough (GB)

(73) Assignee: The Secretary of State for Defence in Her Brittanic Majesty's Government of the United Kingdom of Great Britain and Northern Ireland of Defence Evaluation Research Agency, Farnborough (GB)

( * ) Notice: Subject to any disclaimer, the term of this patent is extended or adjusted under 35 U.S.C. 154(b) by 0 days.

(21) Appl. No.: 09/180,953

(22) PCT Filed: Jun. 10, 1997

(86) PCT No.: PCT/GB97/01555

§ 371 Date: Nov. 18, 1998

§ 102(e) Date: Nov. 18, 1998

(87) PCT Pub. No.: WO97/47958

PCT Pub. Date: Dec. 18, 1997

(30) Foreign Application Priority Data

Jun. 12, 1996 (GB) ................................... 9612241

(51) Int. Cl.⁷ .................................................. G01N 21/71
(52) U.S. Cl. .......................... 436/110; 436/135; 436/172
(58) Field of Search .................................. 436/172, 110, 436/116, 117, 118, 135, 156; 422/52, 80, 81, 83, 89

(56) References Cited

U.S. PATENT DOCUMENTS

| | | | |
|---|---|---|---|
| 3,996,002 | * | 12/1976 | Fine . |
| 4,193,963 | * | 3/1980 | Bruening ............................... 422/52 |
| 4,717,675 | * | 1/1988 | Sievers .................................. 436/103 |
| 5,092,219 | * | 3/1992 | Rounbehler ............................. 86/50 |
| 5,092,220 | * | 3/1992 | Rounbehler ............................. 89/1.1 |
| 5,094,815 | * | 3/1992 | Conboy .................................. 422/52 |
| 5,459,076 | * | 10/1995 | Stamler ................................. 436/116 |

OTHER PUBLICATIONS

Gray P et al: "The Inflamation of Alkyl Nitrate Vapours and the Effect of Inert Diluents" Proceedings of the Royal Society of London A, vol. 200, Feb. 22, 1950, pp. 114–124, XP002040328 cited in the application see p. 114, paragraph 3, see p. 115, paragraph 3, see p. 116, paragraph 4, see p. 121, paragraph 2 see figure 2.

* cited by examiner

Primary Examiner—Jeffrey Snay
(74) Attorney, Agent, or Firm—Nixon & Vanderhye

(57) ABSTRACT

Energetic materials, particularly explosives materials, are detected in samples by heating a mixture of a sample under a reduced pressure of not more than 100 mbar and detecting the chemiluminescent emission therefrom with a suitable light detector, for example a photomultiplier or photodiode. The sample is heated to a temperature in the region of from 300° C. to 500° C., conveniently in a quartz tube furnace placed within a vacuum chamber. The inlet to the tube furnace may be connected directly into the outlet from a gas chromatography apparatus such that individual compounds from a mixture may be detected as they pas sequentially through the chromatography apparatus and into the tube furnace. An inert carrier gas may be used such as nitrogen, argon or helium or a specific gas to enhance the responsiveness of the method for a particular sample material. Apparatus for carrying out the method is also provided.

10 Claims, 5 Drawing Sheets

(a)  (b)

(a)          (b)

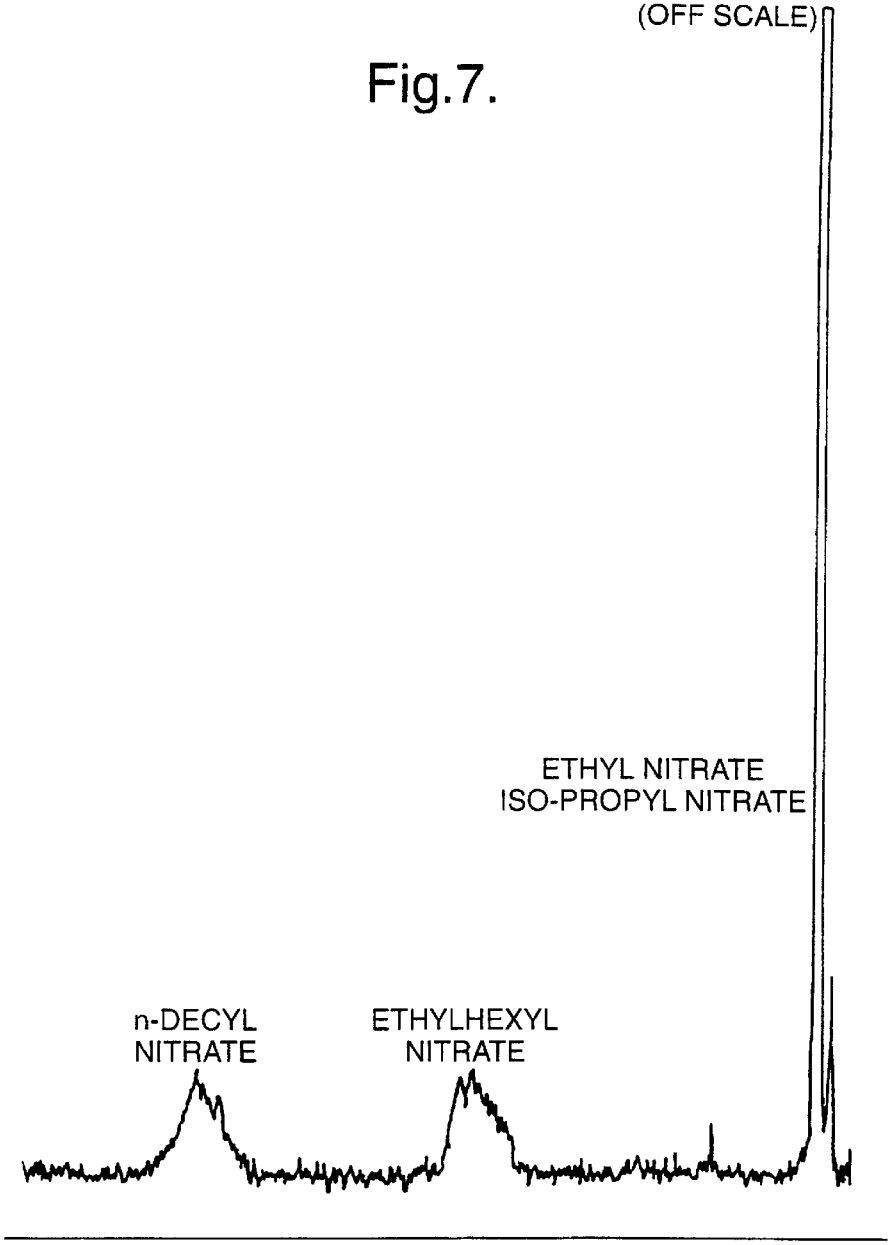
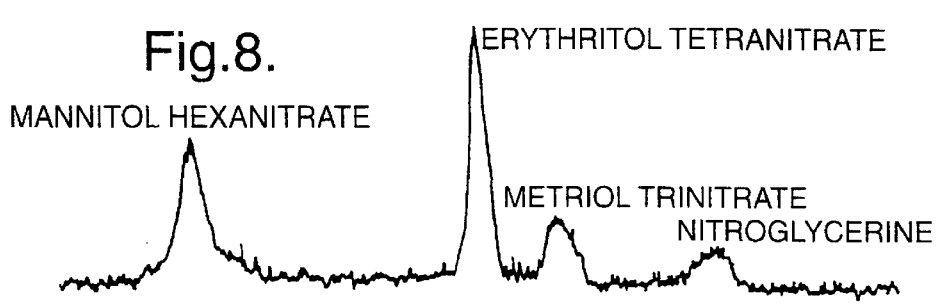

METHOD OF EXPLOSIVES DETECTION

This is a 35 U.S.C. §371 of PCT/GB97/01555, filed Jun. 10, 1997.

This application relates to a method of explosives detection which is based on the technique of chemiluminescence and to an apparatus suitable for carrying out the method.

The technique of chemiluminescence has been employed in determining the concentration of constituents in gaseous sample mixtures. The technique depends on measuring the chemiluminescence generated during reaction of the constituent and an introduced reactant. For example the concentrations of both nitrogen oxide and ozone in gaseous mixtures have been determined by measuring the chemiluminescence produced by the reaction between these two compounds. To do this the mixture containing one of these target species is blended with a known quantity of the other reactant in a well-stirred reactor at relatively low pressures of one Torr or less and the emitted light is detected by, for example a suitable photomultiplier tube and associated current measuring device.

In a particular application of the above general methodology, the phenomenon of chemiluminescence has also been used in the detection of explosives through analysis of the vapours which are given off by such compounds. For example in the method of U.S. Pat. No. 5,092,220, vapours of explosives materials are collected on surfaces coated with gas chromatograph material which trap the explosives vapours but repel nitric oxide. In this way extraneous nitric oxide is eliminated from the sample. The sample vapours are then desorbed and concentrated in one or more cold spot concentrators, after which different vapours are separated by high speed gas chromatography. The individual sample vapours are then decomposed in a pyrolyzer to generate nitric oxide which is fed to a chemiluminescence NO detector where it is mixed with ozone and the resultant radiation detected by a photodetector. The detector is operated at a pressure of 1–2 Torr.

This chemiluminescent equipment is known on the market as a Thermal Energy Analyser (TEA) and the combined system with the gas chromatograph used to give separation of mixtures whose components are to be detected is termed a GC/TEA system.

It will be appreciated that the GC/TEA system described here is quite elaborate and costly to implement. Moreover the chemiluminescent emission for the $NO/O_3$ reaction is in the very near IR region of the spectrum and a number of other chemiluminescent reactions occurring between small molecules which may be present, for example CO, give rise to similar emissions. Consequently spectral filtering has to be employed and the sensitivity of the equipment is reduced.

The aim of the present invention is to provide a method of explosives detection which utilises chemiluminescence while avoiding some of the disadvantages of the prior art systems, in particular their limited selectivity and the complexity of the apparatus involved.

To achieve this, the method of this invention makes use of the earlier observation of Gray and Yoffe (Proc. Royal Soc. A, 200, 1949, pp 114–124) that very dilute mixtures of alkyl nitrate vapours with an inert gas such as argon, emit a blue glow when heated under reduced pressure. The effect was observed over the temperature range 300–500° C. and at pressures of up to about 30 kPa.

The applicant has now appreciated that, employing the phenomenon described by Gray and Yoffe, it is possible to devise a method of detection which relies on the direct chemiluminescent emission of heated molecules of energetic materials such as explosives and propellants without the need to provide any external energetic species to aid the chemiluminescent emission. In consequence of this the method of the invention demonstrates a higher degree of selectivity than prior methods with the possibility of eliminating altogether the need for chromatographic separation prior to admission of samples to the chemiluminescent detector. Additional advantages over the indirect methods which have been previously employed are, firstly, that with emission in the blue region of the spectrum, detection of emission is less affected by thermal noise than is the near IR emission from the $NO/O_3$ reaction. Secondly, the highly specific nature of the effect greatly reduces the need to filter light passing into the photomultiplier and thirdly, a detector employing this principle of operation can be made smaller, more robust and much less expensively than the current type of GC/TEA equipments.

Accordingly, the present invention provides a method for the detection of an energetic material in a sample to be tested which comprises introducing the sample into a chamber wherein the sample is heated while being maintained under a reduced pressure of less than 100 mbar, and detecting any light emitted.

In a preferred method of operation the sample is introduced into the heated chamber together with a carrier gas, conveniently as the output from a gas chromatography apparatus.

In the process according to the invention the temperature of the material in the chamber will be at least about 200° C. dependent upon the substance or substances to be detected. Preferably the temperature is of the order of 300° C. to 500° C., most preferably around 400° C. but it should be observed that the satisfactory temperature operating range varies with the material to be detected, ie according to its responsiveness and, at the higher end of the temperature range, its chemical stability. The above suggested operating temperatures are therefore given by way only of guidance. For example, pentaerithritol tetranitrate (PETN) may be destroyed if it is contained for any significant length of time at temperatures as high as 400° C. whereas it is thought that a higher temperature (approaching 500° C.) is needed to stimulate chemiluminescent emission from trinitrotoluene (TNT) perhaps due to the great strength of the aromatic $C—NO_2$ bond which has to be broken. The skilled addressee will readily understand the requirement to determine an optimum temperature of operation for the detection of any particular substance and the means of so doing.

Likewise the optimum operating pressure again varies according to the nature of the material to be detected. Thus, for example, it has been generally observed that PETN produces a more intense emission at lower pressures (below 10 mbar) within the defined range whilst both cyclotrimethylene trinitramine (RDX) and nitroglycerine (NG) generally give more intense emissions at pressures towards the higher end of the range. Higher pressures are also required for ready observation of emission from ethylene glycol dinitrate (EGDN) and TNT.

Apart from the effects of the temperature and pressure under which the present process is operated in relation to the responsiveness of different materials which it may be desired to detect, the amount of light generated by different substances has been found to vary with the amount of substance introduced into the chamber of the apparatus and also the sensitivity of the detector is found to be to some extent substance dependent. For example generally lower responses have been found for RDX and TNT than for PETN. The responses for particular explosives vary also with the nature of any carrier gas which is present in the chamber.

Thus, although an inert gas such as those in Group 8 of the Periodic Table (helium, neon, argon etc.) or most conveniently nitrogen, may be used as the carrier gas, specific gases may have the ability to enhance the chemiluminescent reaction for a particular sample material. For example, it has been found that the use of methane instead of helium as the carrier gas enhances the response in the case of NG.

Accordingly, the skilled person will readily appreciate that some trialling will be required to determine, for each substance which is to be detected, the preferred operating conditions and, in the case where mixtures of substances are expected to arise, conditions which are a compromise between those most appropriate to the various substances anticipated in the mixture may have to be selected.

The samples may be introduced either neat into the chamber or may be first dissolved in a solvent which will not itself produce any chemiluminescent emission under the conditions employed in the method according to the invention. Solvents which have been found to be satisfactory from this point of view include acetone, ethyl acetate, methanol, ethanol, pentane, hexane, cyclohexane, diethyl ether, petroleum ether, methyl-t-butyl ether or toluene. Tetrahydrofuran is generally unsuitable because of its extreme tendency to form peroxides on exposure to air.

In an alternative mode of operation, the apparatus of this invention will be connected downstream of a gas chromatography equipment such that the output from the latter is fed directly into the detector. In this way individual components of a mixture of substances can be sequentially detected as they exit from the chromatography equipment. In this mode of operation, in order to ensure that substances exiting the GC equipment are not condensed on the walls of the connector placed between the two equipments, it is preferred to provide a means of heating the connector. Typically the injection port into the chamber will be maintained at a temperature of 150° C. to 250° C., most conveniently at about 170 to 180° C.

The process is applicable generally to the class of energetic materials, ie those materials which are capable of undergoing exothermic (energy-releasing) self-reaction on heating. It is in particular applicable to materials containing nitro-groups which constitute a large and important group of explosives and deflagrating materials but also to peroxides. Thus the following substances have been detected using apparatus according to this invention:—ethyl nitrate (EN), n-propyl nitrate (NPN), iso-propyl nitrate (IPN), nitroglycerine, diethylene glycol dinitrate (DEGDN), triethylene glycol dinitrate (TEGDN), glycerol mononitrate, glycerol-1,2-dinitrate, glycerol-1,3-dinitrate, propane-1,2-diol mononitrate, butane-1,2,4-triol trinitrate, 1,3-butane diol dinitrate, butane-2,3-diol dinitrate, erythritol tetranitrate (ETN), metriol trinitrate, pentane-2,3-diol dinitrate, 3-nitropentan-2-ol mononitrate, 2-ethylhexylnitrate, mannitol hexanitrate, 2-ethyl hexane-1,3-diol dinitrate, n-decyl nitrate, diethyl nitramine (DENA), dioxyethyl nitramine dinitrate (DINA), PETN, TNT and RDX. It must be stressed however that the above list is not to be regarded as being exhaustive with respect to those substances which may be detected using the method of this invention.

In another aspect the invention further provides an apparatus for the detection of energetic materials in a sample to be tested which comprises a first chamber at least a part of one wall of which is transparent to visible radiation, means for maintaining said first chamber under reduced pressure, a second chamber located within said first chamber and comprising a substantially tubular member open at one end thereof to the first chamber and having at its other end means whereby a sample may be introduced into said second chamber, said second chamber being so arranged that its open end is aligned opposite the transparent wall of said first chamber, and said apparatus further comprising means for heating said second chamber and means for detecting light emitted from said second chamber through the transparent part of said first chamber.

Conveniently the first chamber of the apparatus will be connected to an appropriate pumping system to create a partial vacuum therein. The second (heated) chamber is preferably a cylindrical tube made of quartz which is sealed to an inlet for samples at one end and is, at its opposite end, open to the first (vacuum) chamber. In this way a sample introduced into the heated chamber or tube at one end is drawn along the tube and out of its other end into the vacuum chamber. The quartz tube which advantageously forms the heated chamber is conveniently surrounded by an electrical heating coil to form a tubular furnace. Alternatively, a thin film of a metal or alloy such as Nichrome, may be deposited on the outer surface of the quartz tube and heating achieved by passing an electrical current through this film. This latter form of furnace tube has the advantage of being more compact and requires a lower current for heating.

By virtue of the heating thus applied to the second chamber and in the presence of energetic materials in the sample which has been injected, a chemiluminescent reaction will occur within that chamber. A window is provided in the wall of the vacuum enclosure opposite the open end of the heated chamber and on the other side of the window is placed a light detector of any convenient type, such as a photodiode, charge-coupled device, photomultiplier tube or spectrometer. Thus any light which is produced by the chemiluminescent reaction in the heated chamber will be directed out of the open end of that chamber and through the window in the vacuum chamber to be detected by the light detector.

In order to improve the selectivity of the photo detector, filters may be placed in the light path between the vacuum chamber and the photomultiplier tube, in particular to prevent longer wavelength IR radiation generated by the furnace passing through to the photomultiplier. Conveniently the window in the vacuum chamber may itself comprise one of the filters.

To provide even greater selectivity and to aid in the identification of the particular explosive material which is causing an emission, the light passing through the window may be led into an optical spectrometer either directly, by way of a system of mirrors and lenses, or through a light pipe. In the latter case the collecting end of the pipe is placed in a light-tight tube or housing attached adjacent the window in the vacuum chamber and arranged to face the window. A lens to focus light passing through the window onto the end of the light pipe is also advantageously provided in the housing at a position close to the window. By means of the spectrometer any discrete part or parts of the total emission spectrum may selectively be detected or the entire spectrum may be registered and plotted as a graph showing light intensity against wavelength.

The furnace chamber may be provided with a further inlet for the supply of eg. nitrogen gas thereto or alternatively the apparatus will be connected to the output from a gas chromatography equipment so as to provide detection of the separated components of a mixture passed from some outside source into the GC equipment as previously described.

When the detector is connected to a gas chromatography apparatus, its responsiveness to different substances may be altered by varying the position of the end of the GC column in relation to the furnace tube and specifically by arranging whether or not the end of the GC column extends into the furnace tube and if so by how much. For PETN, for example, the detector response falls off sharply when the column tip extends by more than about 2 cm into the furnace tube whereas with NG and especially with RDX a stronger response is obtained when the column projects by more than 2 cm into the furnace. This factor thus appears to be related to the optimum temperature for observation of chemiluminescent emission from a particular substance.

In operation of the apparatus of the invention, the gas supply and heater (furnace) are switched on and allowed to stabilise. At the same time the light detection equipment, such as a photomultiplier, is switched on. Once the detector is ready a sample to be tested (either neat or in solution) is injected into the chamber (without use of any carrier gas) and any light emitted by the sample in the chamber is detected by the photomultiplier, the output from which may conveniently be recorded on a chart recorder or the like. Alternatively, where a gas chromatography apparatus is used to provide separation of mixtures in a sample the sample is injected into the chromatograph injection port.

The invention will now be further described with reference to the following examples and to the accompanying drawings in which:

FIGS. 3 to 10 are traces of the output from the photomultiplier showing peaks corresponding to various substances injected into the apparatus of the present invention.

Figure 1:
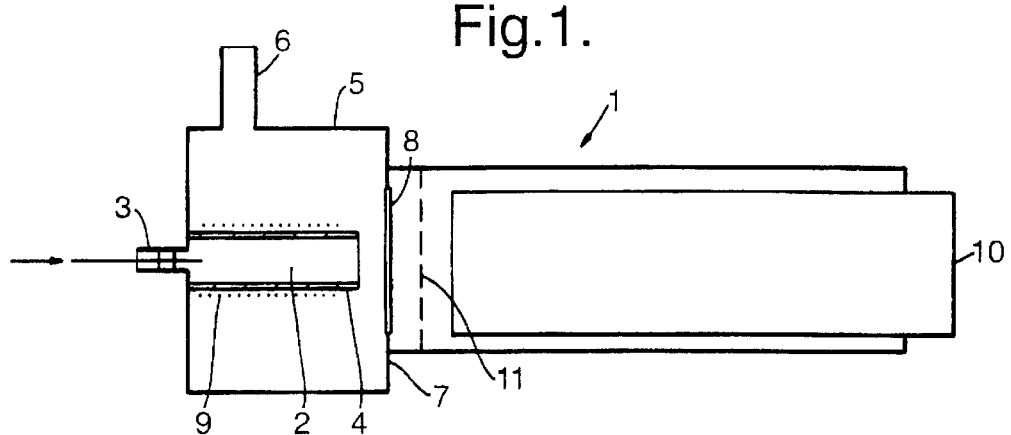
FIG. 1 is a schematic representation of an apparatus according to the present invention connected downstream of a gas chromatography apparatus.
Figure 3:
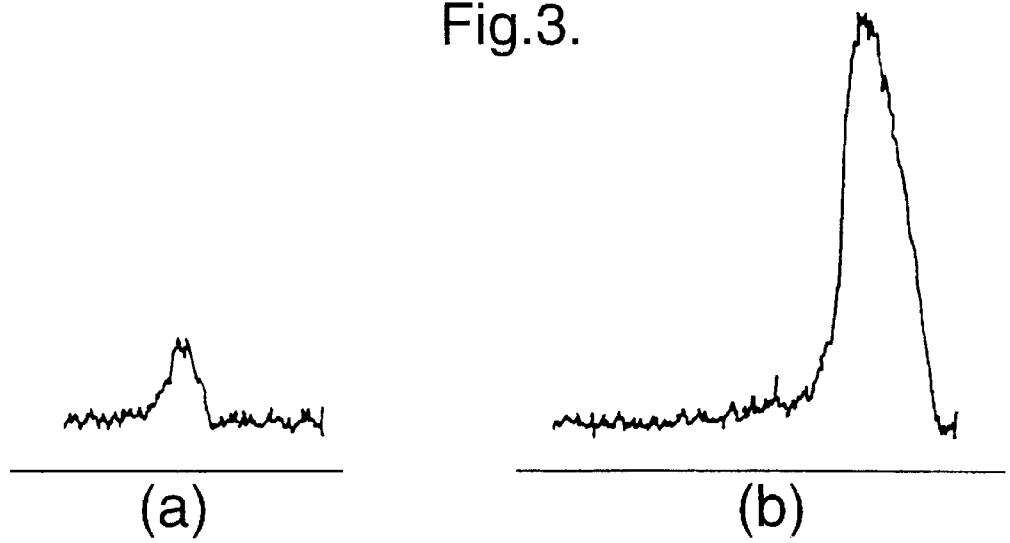
Figure 4:
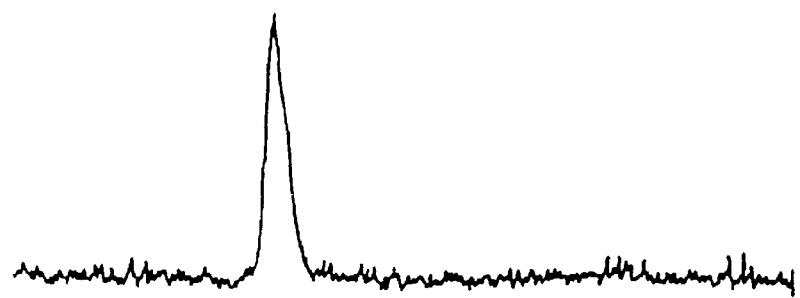

In FIG. 1, a detector according to the present invention is shown generally at 1. It comprises a chamber 2 for the receipt of samples through input 3, the chamber comprising a quartz cylindrical tube 4 which is sealed to the inlet 3 at one end and is open at its other end to a vacuum chamber 5. Chamber 5 is evacuated through outlet 6 by a pump (not shown) and has, in its wall 7 lying opposite the end of tube 4, a window 8 which is transparent to visible light. Surrounding the tube 4 is an electrical heater coil 9, the leads to which are not shown.

A photomultiplier unit 10 is attached to the outside of the vacuum chamber in a position in line with the chamber 2 such that any emission of light within the chamber can be detected by the photomultiplier. Optical and IR filters are placed between chamber 2 and photomultiplier 10. Conveniently one such filter also forms the window 8, in the case of FIG. 1 this is the IR filter and numeral 11 represents an optical filter. Photomultiplier 10 is provided with output leads to an amplifier and chart recorder (not shown) to record electrical output corresponding to light emissions in chamber 2.

Figure 2:
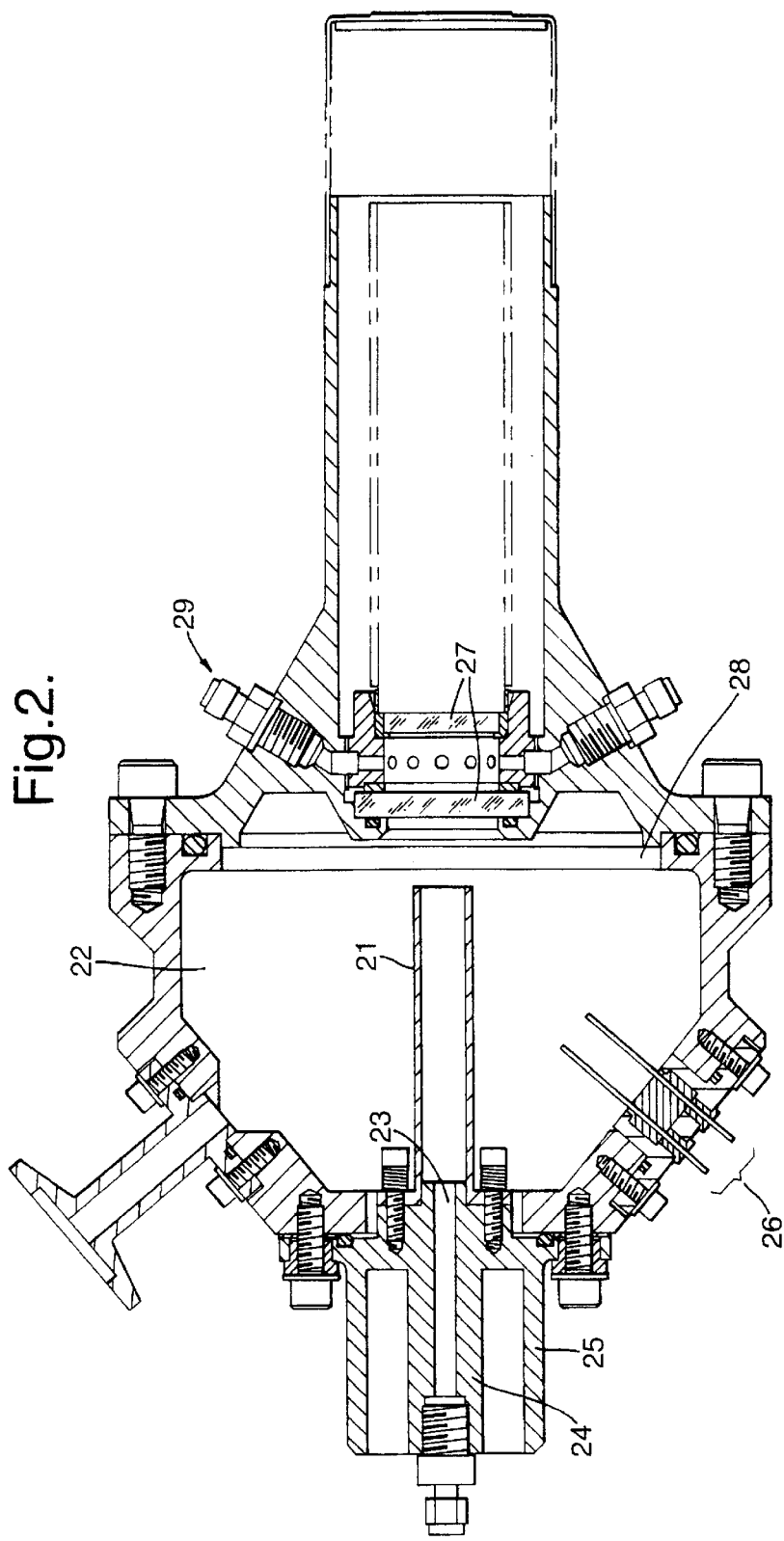
FIG. 2 shows in greater detail an apparatus which is broadly similar to that of FIG. 1.
Figure 5:
Figure 6:

In the apparatus of FIG. 2, a cylindrical quartz tube 21 is located within a vacuum chamber 22 and is sealed to an inlet 23 at one end. In this case the inlet is for substances to be detected in the gas phase after passing through a gas chromatography apparatus. The interface connector 24 between the two apparatus is surrounded by a heated block 25 to obviate the possibility of substances in the gas stream from condensing out on a cold wall. Leads for the electrical heating wires to a resistance heater (not shown) surrounding the tube 21 are at 26. In this embodiment of the invention the photomultiplier tube has IR and visible filters 27 which are separate from the window 28 in the wall of the vacuum chamber 22. The filters are air cooled through inlets one of which is shown at 29.

The apparatus used in the following examples included a quartz tube furnace 7 cm in length by 1 cm diameter heated by a coil of Nichrome resistance wire covered by ceramic cement. The temperature of the furnace was controlled using a thermocouple mounted within the heating coil. The tube furnace was mounted within a vacuum chamber formed of an aluminium casing, vacuum being provided by an Edwards RV3 Rotary vane vacuum pump with an Edwards APG 111M pirani vacuum gauge connected to monitor the chamber pressure. The side of the casing opposite the open end of the furnace was provided with a Pyrex window and a blue filter which limited transmission to the wavelength range 350–460 nm.

The light emissions were fed either to a Thorn EMI Type 9924B17 photomultiplier (PM) or to a Perkin-Elmer LS50B fluorescence spectrometer with a Perkin-Elmer FL Data Manager operating on a DEC 316 computer. The PM signal was amplified by a Carlo Erba Instruments PRD 500 unit and this was connected to a Lloyd Instruments Graphic 1000 chart recorder. For the spectrometer the visible filter used with the photomultiplier was removed and replaced with a lens which focussed light onto the collection end of a light pipe. This pipe, which fed the emissions into the spectrometer, was held in place by a custom made mounting which was designed to allow adjustment of the end of the pipe so as to obtain an optimum position for light collection. The lens was of quartz and allowed transmittance in the UV region. The spectrometer software allowed both scanned spectra (intensity vs wavelength) and timedrives (variation in intensity with time at a fixed wavelength) to be produced.

Measurements without the gas chromatograph used the following conditions:

furnace temperature=400° C.

interface temperature=150° C.

vacuum=1.5 mbar and with the gas chromatograph (for Examples 3 onwards) the conditions were:

furnace temperature=400° C.

interface temperature=170° C.

vacuum=0.2 mbar carrier gas pressure=0.75 kg cm2

GC oven temperature=80° C. for 1 min, then 20° C. to 250° C.

injection port temperature=175° C.

The gas chromatograph used was a Carlo Erba Instruments HGRC 5300 Mega Series fitted with a Chrompack 4 m polyimide clad silica column coated with bonded 7% cyanopropyl-7% phenyl-1% vinyldimethoxysiloxane having a film thickness of 0.21 μm and an i.d. of 0.25 mm. The column was fed through a $\frac{1}{16}$th inch Swagelok fitting (attached to the interface in place of the septum head) and into the detector furnace. The detector was positioned vertically on top of the GC with the interface set down well into the GC oven. Except where otherwise indicated high purity helium was used as the carrier gas.

EXAMPLE 1

Using an apparatus which was generally similar to that illustrated in FIG. 2 but in which the quartz tube also served as the vacuum chamber and was connected downstream of a gas chromatography apparatus, samples of glycerol-1,3-dinitrate, nitroglycerine, glycerol-1,2-dinitrate and ethylhexane-1,3-diol dinitrate in various solvents and in the amounts shown in Table 1 were introduced into the heated chamber. The carrier gas pressure varied between 0.2 and 2 bar for the various samples while the chamber temperature was 400° C. The vacuum as measured by Pirani gauge was in the range 2.0 to 3.0 mbar. The connector was maintained at a temperature of around 175° C. in each case. Use of different amounts of various samples shows the variations in responsiveness of the detector. The photomultiplier outputs for the various samples are shown in FIGS. 3 to 6.

TABLE 1

| Chromatogram number (FIG. ref.) | Compound | Solvent | Amount of solution |
|---|---|---|---|
| 3(a) | Glycerol-1,3-dinitrate | Ethyl Acetate (1.5% solution) | 1 μl |
| 3(b) | " | Ethyl Acetate (1.5% solution) | 5 μl |
| 4 | Nitroglycerine | Methanol (1% solution) | 1 μl |
| 5(a) | Glycerol-1,2-dinitrate | Ethyl acetate (1% solution) | 1 μl |
| 5(b) | " | Ethyl Acetate (1% solution) | 5 μl |
| 6 | Ethylhexane-1,3-diol dinitrate | Acetone (2.6% solution) | 5 μl |

EXAMPLE 2

The same apparatus as used in Example 1 was connected to a GC apparatus and used to detect individual components of specimen mixtures fed to the GC apparatus. The following mixtures were used:

a) EN, IPN, ethylhexyl nitrate and n-decyl nitrate; and
b) NG, erythritol tetranitrate, mannitol hexanitrate and metriol trinitrate.

A carrier pressure of 2.0 bar of nitrogen was used and the interface block was maintained at a temperature of 185° C. The initial GC oven temperature was 40° C. As shown in the trace at FIG. 7, the IPN and EN peaks appeared immediately following injection, whereas the ethylhexyl nitrate peak appeared later as the GC oven temperature reached 65° C. and the least volatile n-decyl nitrate later still when the oven temperature had reached 110° C. In the case of mixture (b) (trace at FIG. 8) conditions were similar to those for (a) except that the initial GC oven temperature was 80° C.

EXAMPLE 3

The apparatus of FIG. 2 was connected to a GC apparatus and used to detect the individual components of a specimen mixture having the following composition (solvent: ethyl acetate):

| | | |
|---|---|---|
| | EGDN | 500 ng/μl |
| | NG | 500 ng/μl |
| | TNT | 50 ng/μl |
| | PETN | 100 ng/μl |
| | RDX | 100 ng/μl |

Figure 9:
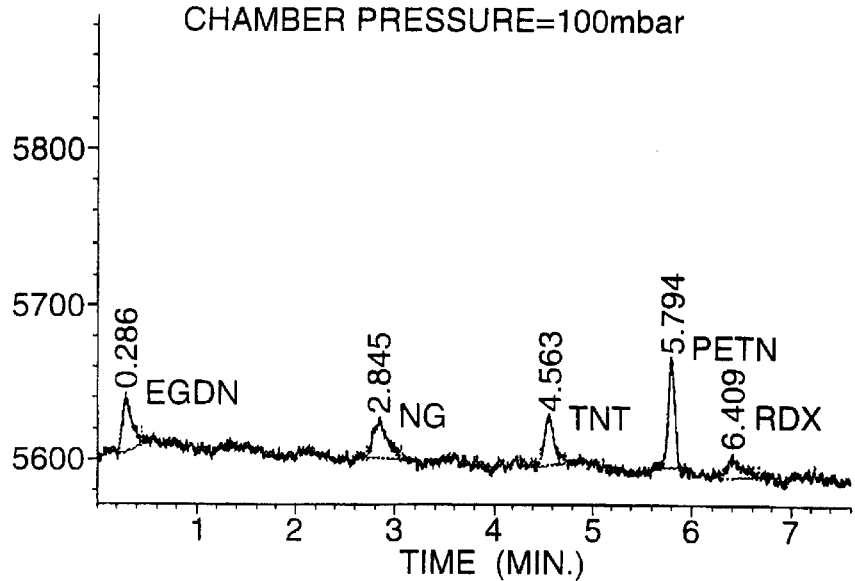

The operating conditions were as stated above and the chamber pressure was 100 mbar, using nitrogen as the carrier gas. From the trace obtained (FIG. 9) it can be seen that all five substances appear. Individual identities were confirmed by running through single component solution samples under the same conditions.

Figure 10:
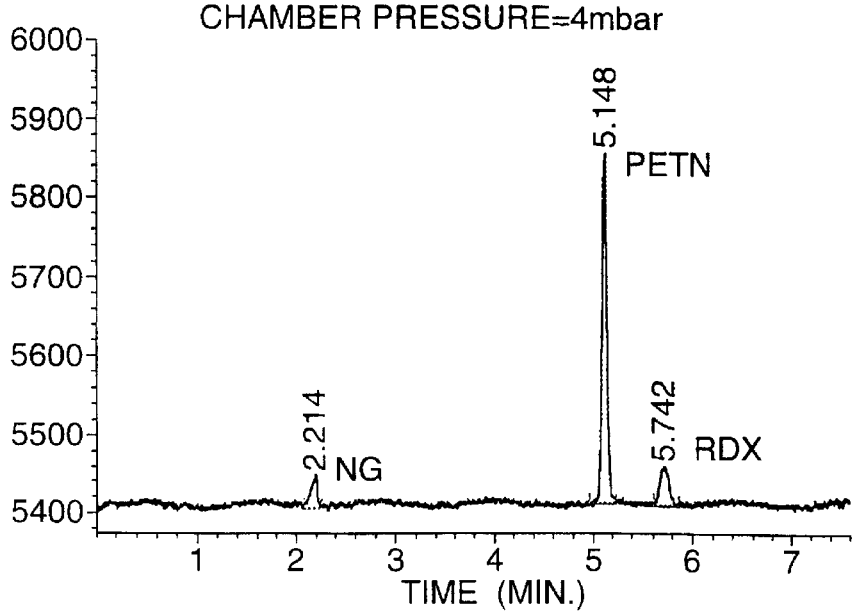

With both hydrogen and helium as the carrier gas neither EGDN nor TNT were observed at a chamber pressure of 4 mbar but a good response was obtained for PETN in particular (FIG. 10).

EXAMPLE 4

Using the same conditions and equipment as for Example 3 (except that the GC oven temperature programme was started from 40° C. and that the vacuum was 3 mbar), a 1 μl injection of 0.01% solution of triacetone triperoxide (TATP) in acetone produced a strong peak at just under 1 minute. This indicates an initial detection limit of less than 100 ng. Similarly a solution of diacetone diperoxide (DADP) (0.1% in ethyl acetate) gave a very sharp peak after 0.25 minute.

What is claimed is:

1. A method for detecting an energetic material in a sample to be tested, which method comprises introducing the sample into a chamber, heating the sample while maintaining it under a reduced pressure of less than 100 mbar, and detecting any light emitted, the method conducted in the absence of any external energetic species.

2. A method for detecting an energetic material capable of undergoing exothermic self-reaction or heating in a sample to be tested, which method comprises the steps of (a) introducing the sample into a chamber, (b) heating the sample while maintaining it under a reduced pressure of less than 100 mbar, and (c) detecting any light emitted, the method conducted in the absence of any external energetic species.

3. A method according to claim 1 or 2 wherein the chamber is heated to a temperature of from about 300° C. to about 500° C.

4. A method according to claim 1 or 2 wherein the pressure within the chamber is maintained at or below 20 mbar.

5. A method according to claim 1 or 2 wherein the sample is carried in a gas stream into the chamber.

6. A method according to claim 5 wherein the sample and gas stream comprise an output from a gas chromatography apparatus.

7. A method according to claim 5 wherein the gas is an inert gas.

8. A method according to claim 7 wherein the inert gas is selected from the group consisting of helium, argon and nitrogen.

9. A method according to claim 1 or 2 wherein the material to be detected is a peroxide.

10. A method for detecting an explosives material capable of undergoing exothermic self-reaction or heating in a sample to be tested, which method comprises the steps of (a) introducing the sample into a chamber, (b) heating the sample while maintaining it under a reduced pressure of less than 100 mbar, and (c) detecting any light emitted, the method conducted in the absence of any external energetic species.

* * * * *